United States Patent [19]

Gratton

[11] Patent Number: 4,840,485

[45] Date of Patent: Jun. 20, 1989

[54] FREQUENCY DOMAIN CROSS-CORRELATION FLUOROMETRY WITH PHASE-LOCKED LOOP FREQUENCY SYNTHESIZERS

[75] Inventor: Enrico Gratton, Urbana, Ill.

[73] Assignee: I.S.S. (U.S.A.) Inc., Champaign, Ill.

[21] Appl. No.: 225,595

[22] Filed: Jul. 27, 1988

Related U.S. Application Data

[63] Continuation of Ser. No. 943,253, Dec. 17, 1986, abandoned.

[51] Int. Cl.[4] ............................................. G01N 21/64
[52] U.S. Cl. .................................. 356/317; 250/458.1
[58] Field of Search ...................... 356/317, 318, 417; 250/458.1, 459.1, 461.1, 461.2

[56] References Cited

U.S. PATENT DOCUMENTS 3,886,370  5/1975  Schubert et al. ..................... 250/552
4,594,511  6/1986  Cooper et al. ....................... 356/318

OTHER PUBLICATIONS

"MOS Replaces Crystal IC as Synthesizer," *Electrotechnolgoy*, vol. 5, No. 3, p. 73, Jul. 1977.
Giles, T. G., "Versatile LSI Frequency Synthesizer System", *Electronic Components and Applications*, vol. 2, No. 2, Feb. 1980, pp. 91–94.
Marconi Instruments 10 kHz to 1000 MHz AM/FM Signal Generator 2022—Issue 1 8/84 (Brochure).
Syntest Corporation Data Sheet SM-105 Brochure.
Industria Strumentazioni Scientifiche—I.S.S. Greg 200 Multifrequency Cross-Correlation Phase and Modulation Fluorometer (Brochure).
Chemical Physics Letters—vol. 119, No. 2,3 (pp. 217–222) Aug. 30, 1985.
The Journal of Biological Chemistry—1984 by The American Society of Biological Chemists, Inc. entitled: Detection of Phospholipid Phase Separation, vol. 259, No. 22 Issue of Nov. 25, pp. 14011–14017, 1984.
E. Gratton & B. Barbieri entitled: Multifrequency Phase Fluorometry Using Pulsed Sources: Theory and Applications—28 Spectroscopy, vol. 1, No. 6 —pp. 28–38.
Enrico Gratton et al. entitled: Multifrequency Phase and Modulation Fluorometry—Ann. Rev. Biophys. Bioeng. 1984, 13:105–124.
David M. Jameson et al.—entitled: The Measurement and Analysis of Heterogeneous Emissions by Multifrequency Phase and Modulation Fluorometry—Applied Spectroscopy Reviews, 20(1), 55–106 (1984).
E. Gratton et al., entitled: A Continuously Variable Frequency Cross-Correlation Phase Fluorometer with Picosecond Resolution, Biophysical Society , vol. 44, Dec. 1983, pp. 315–324.
Tiziana Parasassi et al., entitled: Study of Heterogeneous Emission of Parinaric Acid Isomers Using Multifrequency Phase Fluorometry—1984 American Chemical Society, pp. 5660–5664.
Tiziana Parasassi et al., entitled: Time–Resolved Fluorescence Emission Spectra of Laurdan in Phospholipid Vesicles by Multi–Frequency Phase and Modulation Fluorometry—Cellular and Molecular Biology 32(1), 103–108, 1986.
Enrico Gratton et al., entitled: New Approach to Phase and Modulation Resolved Spectra—1985 American Chemical Society—Analytical Chemistry, vol. 57, No. 8, Jul. 1985, pp. 8–11.
E. Gratton et al., entitled: Multifrequency Cross–Correlation Phase Fluorometer Using Synchrotron Radiation—American Institute of Physics Rev. Sci. Instrum., vol. 55, No. 4, Apr. 1984, pp. 486–494.
J. Ricardo Alcala et al., entitled: A Multifrequency Phase Fluorometer Using the Harmonic Content of a Mode–Locked Laser—Analytical Instrumentation, 14(3&4), 225–250 (1985).

*Primary Examiner*—F. L. Evans
*Attorney, Agent, or Firm*—Garrettson Ellis

[57] ABSTRACT

Frequency domain cross-correlation fluorometers may be improved over present designs by providing a coherent signal at one frequency to means for detecting luminescence from a sample, which is elicited by light modulated at another frequency, in which the two frequencies, obtained from a pair of phase-locked loop frequency synthesizers, are different from each other by at least 100 hertz, which is a significantly greater difference than used in corresponding prior art fluorometers. This permits the use of the phase-locked loop frequency synthesizers, rather than the currently used direct synthesis synthesizers, providing significant advantages.

9 Claims, 1 Drawing Sheet

FREQUENCY DOMAIN CROSS-CORRELATION FLUOROMETRY WITH PHASE-LOCKED LOOP FREQUENCY SYNTHESIZERS

This is a continuation of application Ser. No. 943,253, filed on Dec. 17, 1986 now abandoned.

BACKGROUND OF THE INVENTION

Frequency domain cross-correlation fluorometry is a known process by which excited light is modulated at a given frequency. The phase shift and the modulation ratio of emission with respect to excitation are measured to obtain the lifetime of the excited state, making use of the cross-correlation technique. This is a versatile tool for determining many subtle characteristics of matter and their interactions. See, for example, the article by E. Gratton and B. Barbieri entitled Multifrequency Phase Fluorometry Using Pulsed Sources: Theory and Applications; Spectostropy, Vol. I, No. 6, pp. 28–38 (1986). See also the article by Gratton, Jameson & Hall entitled Multifrequency Phase and Modulation Fluorometry; Ann. Rev. Biophys. Bioeng. Vol. 13, pp. 105–124 (1984). See also the article by Gratton and Limkeman entitled A Continously Variable Frequency Cross-Correlation Phase Fluorometer With Picosecond Resolution, Biophysical Journal, Vol. 44, pp. 315, 324 (1983). The above articles are given by way of example only, with other articles being available as well.

Fluorometers having continuous frequency domain cross-correlation fluorometric function are commercially available from I.S.S. Inc. of Champaign, Ill., such fluorometers being sold under the trademark GREG. Such a device is capable of measuring and analyzing excitation and emission spectra, fluorescence decays, phase and modulation resolved spectra, time-resolved spectra, and the dynamic depolarization of various materials. As is well known, the apparatus has a highly collimated xenon arc lamp for steady-state measurements and routine lifetime determinations, plus a laser source (UV-visible) for lifetime measurements requiring extremely high sensitivity and accuracy. The modulation of the excitation light is obtained using a wide band electro-optical modulator, specifically a Pockels cell. The Pockels cell is modulated by a direct synthesis frequency synthesizer which provides a signal to the Pockels cell at a first frequency. Another direct synthesis synthesizer provides a signal, in phase coherence with the first synthesizer by driving the two synthesizers from the same quartz crystal. This second synthesizer provides a signal at a second frequency, different from the first frequency, to a pair of detector units set up for detecting luminescence in the sample generated by the modulated light source.

The signal at the output of the detector unit contains a component which is of a frequency that is the difference between the two frequencies, which difference is named the "cross-correlation frequency". The cross-correlation frequency is filtered and processed by a data acquisition unit to provide both the phase shift and the modulation difference of the luminescence of the sample, when compared with the modulated excitation light directed at the sample.

The electronic circuits are designed to filter and process the cross-correlation frequency component only. At the present time, only cross-correlation frequencies of 25 hertz, 31 hertz, and 40 hertz are used. Appropriate phase coherence at these low frequencies are obtained by use of the direct synthesis frequency synthesizers which have a resolution of 1 hertz.

It would be desirable to use phase-locked loop frequency synthesizers because their cost per unit is currently at least two thousand dollars less than each direct synthesis synthesizer unit. However, their use has been, up to the present time, impractical due to the phase noise of the cross-correlation frequencies used in the prior art.

In accordance with this invention, apparatus for frequency domain cross-correlation fluorometry is provided which utilizes phase locked-loop frequency synthesizers. For this reason alone, the cost saving in the apparatus, when compared with the use of direct synthesis synthesizers, may currently be at least four thousand dollars per unit and very probably more than that. Furthermore, phase-locked loop synthesizers operate in a larger frequency range, which increases the lifetime range measurable using cross-correlation frequency domain fluorometers. Moreover, the electronic filter that separates the cross-correlation frequency component of the output signal is cheaper than the corresponding electronics involved with the direct synthesis synthesizers, and is of easier construction. Additionally, the improvements of this invention allow faster measurements, with reduced dead time between two consecutive measurements. This, in turn, greatly facilitates the possibilities in studies of lifetime kinetics measurements.

DESCRIPTION OF THE INVENTION

In accordance with this invention, apparatus for frequency domain cross-correlation fluorometry is provided, which comprises: a source of electromagnetic radiation and means for amplitude modulating the electromagnetic radiation at a first frequency. Means are also provided for directing the amplitude-modulated electromagnetic radiation at a sample to cause the sample to respond by luminescence (typically fluorescence), plus means for detecting such luminescence.

A signal is also provided to modulate the gain of the detecting means, which signal is coherent with the amplitude modulating means and is at a second frequency, different from the first frequency. Preferably, both the amplitude modulating means and the means for providing the signal at the second frequency each comprise a phase-locked loop frequency synthesizer. The synthesizers operate coherently with each other, typically off of a single quartz crystal in one of the synthesizers, with the other synthesizer acting in slave relationship to the first synthesizer.

In accordance with this invention, the second frequency is different from the first frequency by at least 100 hertz, a significant increase over the frequency difference used in apparatus of the prior art. Specifically, it is preferred for the signal difference to be from 500 to 2,000 hertz, and generally no more than 5000 hertz.

Means are also provided for deriving a resultant signal from the electromagnetic radiation and the detecting means at a frequency of the difference between the first and second frequencies. This resultant signal may be processed through conventional electronics and a computer, in a manner similar to the prior art apparatus, to detect phase shift and modulation changes of the luminescence when compared with the electromagnetic radiation. Typically, the detecting means is a photomultiplier, having the second frequency imposed upon it by one of the phase-locked loop frequency synthesizers, to modulate the gain of the photomultiplier at the second frequency. The resulting product of the signal of the first frequency, and of the gain of the detecting means at the second frequency, provides a component at a frequency that is the difference between the two frequencies (the cross-correlation frequency) which is filtered by conventional electronics to measure phase shift of the emission and the modulation of the emission; specifically, the ratio between the modulation of the emission and the modulation of the electromagnetic radiation used to produce the emission.

By this technique, deep insights into the structure and interactions of matter can be obtained.

Phase-locked loop frequency synthesizers are well known to the art. See, for example, the fifth edition of the book by Robert L. Schrader entitled Electronic Communication, pp. 222-224. Basically, in a phase-locked loop frequency synthesizer, a stable (and typically crystal) reference oscillator AC, and the AC from an oscillator having a frequency which can be varied by a DC voltage applied to it, are both fed to a phase detector circuit. If the frequency and phase of the reference and voltage-controlled oscillator signals are equal, the DC output voltage from the phase detector will be some particular value. This DC is fed through a low pass filter to a DC amplifier and to the voltage input circuit of the voltage controlled oscillator. If the voltage-controlled oscillator tries to shift off frequency, the phase detector develops a change in the DC "error" voltage which corrects the voltage-controlled oscillator frequency and locks it to the reference frequency again. The voltage-controlled oscillator frequency is corrected not only to exactly the frequency of the reference AC, but to the same phase. One locked in, changes of the reference oscillator frequency are tracked by the voltage-controlled oscillator units. Further, well-known details of the phase-locked loop frequency synthesizer are available in the previously cited reference and elsewhere. Phase-locked loop synthesizers are available, for example, from the Syntest Corp. of Marlboro, Mass., or Marconi Instruments of Allendale, N.J.

DESCRIPTION OF SPECIFIC EMBODIMENT

Figure 1:
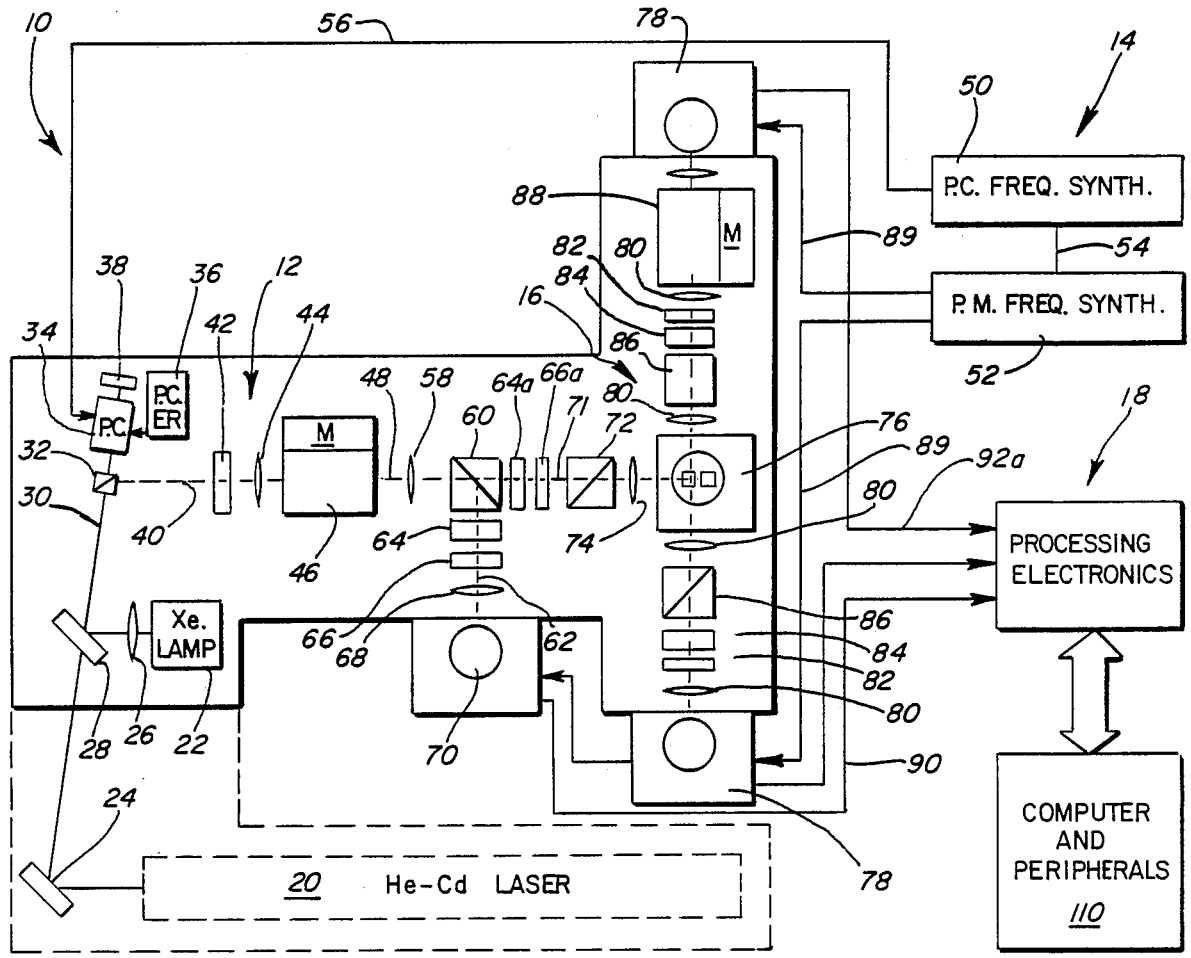
FIG. 1 is a diagrammatic view of a cross-correlation frequency domain fluorometer, improved in accordance with this invention.

Referring to the drawings, the apparatus of this invention may constitute, for example, a GREG 200 multifrequency cross-correlation phase and modulation fluorometer sold by ISS Inc. of Champaign, Ill., with only those modifications as described herein. Alternatively, other designs of fluorometry machines may use the invention of this application as well.

Cross correlation frequency domain fluorometer 10 may comprise four major components: intensity-modulated light source unit 12, frequency generator unit 14, optical module 16 including the sample holder and the light detectors, specifically the photomultiplier units, and data acquisition unit 18.

A light source of unit 12 may be a laser 20, for example a Liconix 4207 NB He-Cd laser. A xenon lamp 22 is provided as an alternate light source in the specific apparatus shown. Alternatively, synchroton radiation or mode-locked lasers may be used for studies of high criticality.

Laser light is reflected from mirror 24, or, alternatively, the output of arc lamp 22 is focused through lens 26 and reflected off of mirror 28, to cause light beam 30 to pass through two-way polarizer 32 and through Pockels cell 34. If laser 20 is used, mirror 28 is removed.

Two-way polarizer 32 may be of the Glan-Taylor type, while the Pockels cell may be a LASERMETRICS 1042 Pockels cell. Pockels cell 34 may be controlled by power unit 36.

Light beam 30 passing through Pockels cell 34 is reflected from mirror 38 back through the Pockels cell, being deflected by two-way polarizer 32 along light path 40, through electronic shutter 42, lens 44, and motor driven monochromator 46, so that emergent light beam 48 may be of essentially a single color or wavelength, typically in the near ultraviolet or visible (180 nanometers to 800 nanometers). The selection of the wavelength depends, of course, upon the absorbancy of the material to be studied.

Frequency unit 14 comprises a pair of phase-locked loop frequency synthesizers 50, 52. Synthesizers 50, 52 are electrically connected by lead 54, and conventionally driven in coherent manner off the same quartz crystal positioned in one of the synthesizers, to produce first and second signals having a frequency difference of, in this specific case, one kilohertz.

Synthesizer 50 provides an output frequency through conductor 56 to Pockels cell 34, to impose upon the light beam passing through it an amplitude modulation at a corresponding frequency. In the particular apparatus shown, the frequency is highly variable and adjustable, typically ranging from 10 kilohertz to 1000 megahertz, and higher as desired, this frequency corresponding to the first frequency described above.

Thus, light beam 48 is both amplitude modulated and monochromatic after leaving monochromator 46. It passes through lens 58 and beam splitter 60, to provide a pair of beams. One beam 62 passes through filter 64, when such is desired, shutter 66, and lens 68, to impinge reference detector 70. This and all the detectors present may be Hamamatsu R928 photomultipliers.

The other split beam 71 passes through a corresponding filter 64a, shutter 66a, Glan-Taylor polarizer 72, and lens 74, to impinge upon a sample in sample holder 76. There, the fluorescence or luminescence of the sample material is elicited in conventional manner by irradiation. The resultant fluorescence may be directed to a pair of emission detectors 78 along a pair of different beam paths, each path including, respectively, lenses 80, manual shutters 82, optional filters 84, and Glan-Taylor polarizers 86. One of the beam paths, as shown, may include a second motor driven monochromator 88.

Second frequency synthesizer 52 provides a signal at a second frequency through conductors 89 to modulate the gain of detectors 78. The second frequency is, specifically, one kilohertz apart from (either greater or less) the first frequency from synthesizer 50, with both frequencies being adjustable together while maintaining their one kilohertz difference.

The processing electronics 18 are typically formed on a single card, and are connected to reference detector 70 through conductor 90 and to each of detectors 78 through conductors 92 and 92a.

Figure 2:
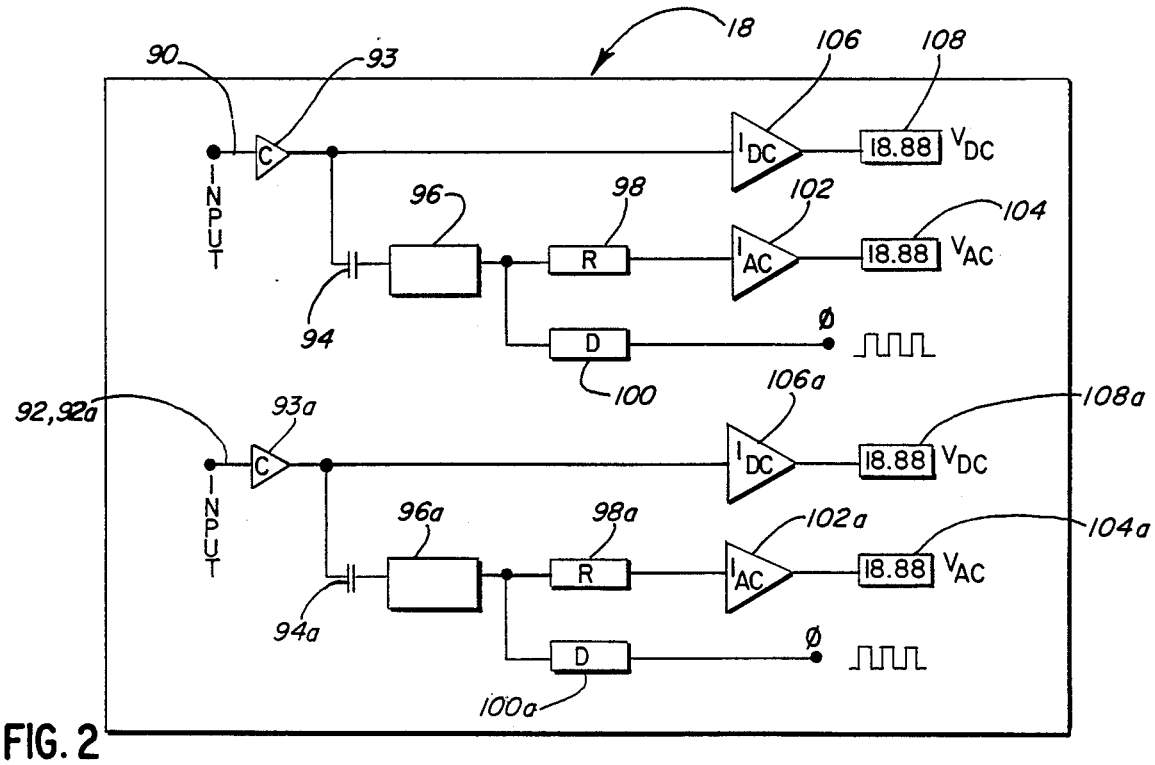
FIG. 2 is a flow diagram of the analog electronics of the device of FIG. 1.

As shown in FIG. 2, processing electronics 18 include two identical channels: one for the signal from reference detector 70 through conductor 90, and the other for the signal from the detector 78 which detects the fluorescence through conductor 92 and 92a. If desired, a third independent channel for one of the detectors 78 may be provided, but it is generally contemplated to use the detectors in alternative manner, or with their outputs through conductors 92, 92a connected together.

The signal coming into the input of each channel has an AC and a DC component, in view of the frequencies imposed on the various signals in the system by frequency synthesizers 50, 52. The signal passes through current to voltage converter 93, 93a, with the AC component of the signal being fed through capacitors 94, 94a, and then through a 1 kilohertz filter 96, 96a (typically A.P. Circuit Corp., New York City). The signal is then fed to an RMS converter 98, 98a, and the input to RMS converter 98, 98a is connected to a zero crossing detector 100, 100a. The signal from RMS converter 98, 98a is fed through amplifiers 102, 102a and to voltmeter 104, 104a. The signal from zero-crossing detector 100, 100a forms a square wave for phase measurement.

Simultaneously, the direct current component is fed through DC integrator 106, 106a, and to direct current voltmeter 108, 108a. The four digital voltmeters 104, 104a, 108, 108a, are provided for continuous monitoring of the DC and AC parts of the signals from the respective photomultipliers 70, 78. The results of this monitoring are conveyed to computer and peripherals 110, typically an Apple 2E or IBM PC personal computer with dual disc drive and graphic printer. Commercially available programs can provide interpretation of the data received for analysis of a wide variety of physical phenomena. The use of a typically one kilohertz filter for filters 96, 96a, corresponds with a one kilohertz difference in the frequency of the signals emitted by synthesizers 50, 52.

As the result of this, it becomes possible to use phase-locked loop frequency synthesizers as generators of the necessary phase-coherent signals for cross-correlation frequency domain fluorometry. Currently, savings of at least four thousand dollars per unit can be achieved over prior designs by the replacement of the direct synthesis synthesizers of the prior art in this unit. It can be seen that synthesizers 50, 52 may be operated at other differential frequencies than 1 kilohertz as described above, in that circumstance, filters 96, 96a will be correspondingly modified.

The above has been offered for illustrative purposes only, and is not intended to limit the scope of the invention of this application, which is as defined in the claims below.

That which is claimed is:

1. Apparatus for cross-correlation frequency domain fluorometry, which comprises:
   a source of electromagnetic radiation;
   means for amplitude modulating the electromagnetic radiation at a first frequency;
   means for directing the amplitude-modulated electromagnetic radiation at a sample;
   means for detecting the luminescence of the sample;
   means for providing a signal coherent with amplitude modulated signals produced by said amplitude modulating means, at a second frequency, to said detecting means;
   means for modulating the gain of said detecting means by said signal;
   said amplitude modulating means and means for providing a signal at a second frequency each comprising a separate phase-locked loop frequency synthesizer;
   said second frequency being different from said first frequency by at least 100 hertz; and means for deriving a resultant signal from said electromagnetic radiation and said detecting means at a frequency of the difference between said first and second frequencies, to detect phase shift and modulation changes of said luminescence from that of said electromagnetic radiation.

2. The apparatus of claim 1 in which the difference between said first and second frequencies is no less than 500 hertz.

3. The apparatus of claim 2 in which said first and second frequencies differ by 500 to 2000 hertz.

4. The apparatus of claim 1 in which said means for amplitude modulating the electromagnetic radiation at a first frequency includes Pockels cell means, driven by one of said phase-locked loop frequency synthesizers.

5. A method for frequency domain cross-correlation fluorometry, which comprises the steps of:
   providing a source of electromagnetic radiation;
   amplitude modulating the electromagnetic radiation at a first frequency with a Pockels cell driven by a phase-locked loop frequency synthesizer;
   directing the amplitude-modulated electromagnetic radiation at a sample;
   detecting with a detector the luminescence of the sample while modulating the gain of said detector with a signal at a second frequency to said detector; with said signal at a second frequency being coherent with the modulation of said electromagnetic radiation and said second frequency being different from said first frequency by at least 100 hertz; and
   deriving a resultant signal from said electromagnetic radiation and said detector at a frequency of the difference between said first and second frequencies, to detect phase shift and modulation of said luminescence from that of said electromagnetic radiation.

6. The method of claim 5 in which the difference between the first and second frequencies is no less than 500 hertz.

7. The method of claim 6 in which said first and second frequencies differ by 500 to 2000 hertz.

8. The method of claim 7 in which said electromagnetic radiation is modulated at said first frequency by Pockels cell means, driven by a phase-locked loop frequency synthesizer.

9. The method of claim 8 in which the gain of said detector is modulated at the second frequency by the signal from a phase-locked loop frequency synthesizer.

* * * * *